(12) United States Patent
Taylor et al.

(10) Patent No.: US 7,159,842 B1
(45) Date of Patent: Jan. 9, 2007

(54) MAGNETICALLY-COUPLED ACTUATING VALVE ASSEMBLY

(75) Inventors: Marc D. Taylor, Columbus, OH (US); Michael L. Haynes, Columbus, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 36 days.

(21) Appl. No.: 11/153,278

(22) Filed: Jun. 15, 2005

(51) Int. Cl.
*F16K 31/04* (2006.01)
(52) U.S. Cl. .................................. 251/129.13
(58) Field of Classification Search ........... 251/129.11, 251/129.12, 129.13
See application file for complete search history.

(56) References Cited

U.S. PATENT DOCUMENTS

| | | | |
|---|---|---|---|
| 4,072,800 A | 2/1978 | Gammer | 429/97 |
| 4,809,742 A * | 3/1989 | Grau | 251/129.11 |
| 5,248,570 A | 9/1993 | Meier | 429/121 |
| 5,931,142 A * | 8/1999 | Gerling | 251/129.12 |
| 6,352,144 B1 * | 3/2002 | Brooks | 251/129.17 |

* cited by examiner

*Primary Examiner*—John Bastianelli
(74) *Attorney, Agent, or Firm*—Standley Law Group LLP

(57) ABSTRACT

A magnetically-coupled actuating valve assembly. The actuating valve can be used to control the action of an actuator, such as a hydraulic or pneumatic cylinder. The valve assembly is especially well-suited to use with a damping cylinder of an electronically controlled prosthetic knee. A drive motor is coupled to and actuates a valve body portion of the assembly by means of magnetic attraction and, therefore, the valve assembly operates without the need to physically couple the drive motor to the valve body. The design of the present invention can reduce or eliminate working fluid leaks typically associated with a physical coupling. The design of the present invention may also obviate the need to submerge the drive motor in the working fluid, which typically reduces motor efficiency and may pose a fire hazard.

114 Claims, 6 Drawing Sheets

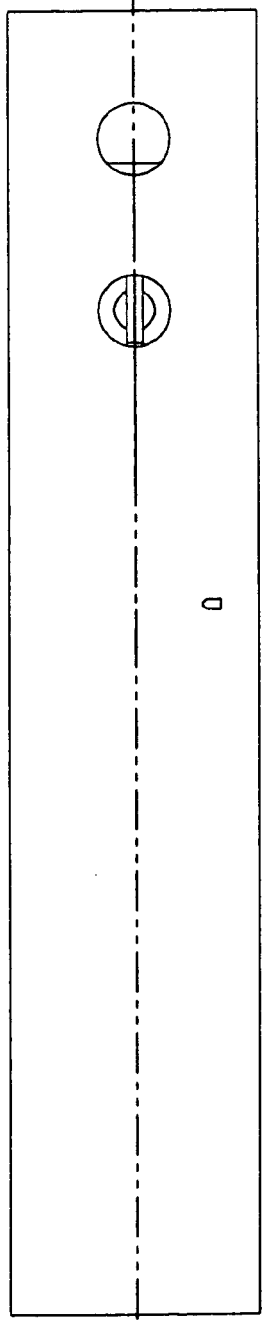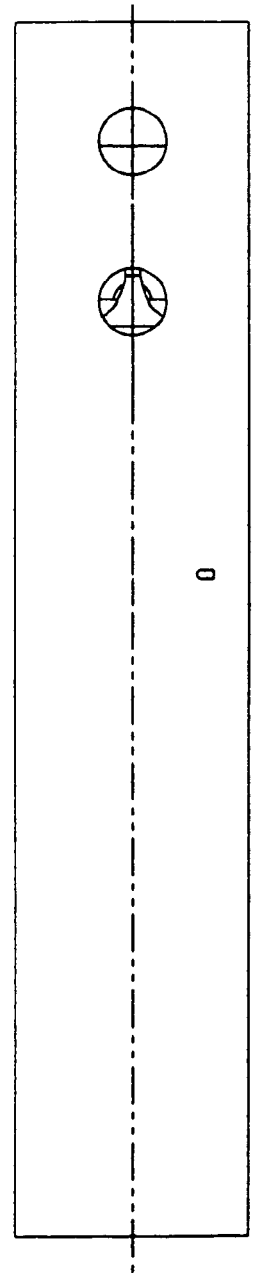
FIG. 1a
FIG. 1b

MAGNETICALLY-COUPLED ACTUATING VALVE ASSEMBLY

BACKGROUND OF THE INVENTION

The present invention is directed to a magnetically-coupled actuating valve assembly for use in controlling an actuator, such as a hydraulic or pneumatic actuator. More specifically, the present invention is directed to an actuating valve assembly having a valve body that is magnetically coupled to a drive motor, thereby allowing the drive motor to be isolated from pressurized fluid passing through the valve assembly.

While it is to be understood that an actuator incorporating the actuating valve assembly of the present invention may be used in a variety of devices, the actuating valve assembly is particularly well-suited to use in an electronically controlled actuator for a prosthetic limb. More particularly, the valve assembly of the present invention is especially compatible with a damping cylinder of an electronically controlled prosthetic knee. Such a damping cylinder can be used to control (damp) the flexion and extension phases of knee movement during the gait cycle of an amputee.

Simple above-knee (AK) prostheses have been constructed with a hinged joint connecting a lower leg portion to an upper leg portion which, in turn, fits over the amputee's residual limb. Such a prosthetic limb allows the amputee to swing the lower leg portion forward during the extension portion of the gait cycle, and also allows for the lower leg portion to fold backward during the flexion portion of the gait cycle. Such simplistic artificial knee joints are problematic, however. For example, failure to fully swing the lower leg portion forward during the extension portion of the gait cycle can result in instability, as the knee joint may bend undesirably under the amputee's weight. In addition, the subsequent flexion of the joint relies solely on energy transfer from the gait cycle. Such knee joint operation can be very difficult for the amputee to control—especially as energy (and momentum) builds up during the gait cycle.

In an attempt to stabilize and control the gait cycle of an AK prosthetic limb, pneumatic and hydraulic damping cylinders have been utilized. These devices are used to damp energy generated during the gait cycle so that the prosthetic limb moves through its range of motion in a more controlled manner. Such damping cylinders can be designed and/or adjusted based on an amputee's weight, gait pattern, and activity level, among other factors. Prosthetic limbs employing such damping cylinders are an improvement over earlier limbs that used only undamped knee joints, however, they generally only allowed the amputee to walk well at one speed.

To further improve the performance of prosthetic limbs having damped knee joints, electronic control systems may be employed. These electronic control systems are in communication with a valve assembly or some other means of controlling the damping cylinder. For example, the valve assembly will typically employ a valve spool (body) or similar mechanism that interacts with various ports in the cylinder housing and allows for control over a flow of hydraulic or pneumatic fluid. A drive motor or some other type of actuator is generally used to shift the valve body or otherwise activate a flow control mechanism. The drive motor or other actuator may be located externally of the housing, or may be placed within the housing.

One problem with using such a valve assembly arises, however, due to the high working fluid pressures that are often present in the damping cylinder(s) that are controlled by the valve assemblies. For example, when locating a drive motor or other actuator externally to the housing, a connector, such as a shaft, must be provided to couple the actuator to the valve body. One or more seals must be located around the connector to prevent leakage of the working fluid to the outside of the cylinder. Because of the high working fluid pressures within the housing, these seals are prone to leakage, which can be quite problematic when the cylinder is used with a prosthetic limb. And, locating a drive motor or other powered actuator within the valve body does not overcome the aforementioned problem, as a seal must still be used around the wiring providing power thereto. Additionally, locating a drive motor in the working fluid generally results in reduced motor power and efficiency and, depending on the particular working fluid involved, may create a fire hazard.

SUMMARY OF THE INVENTION

The present invention overcomes the aforementioned deficiencies by allowing a drive motor to be magnetically coupled to a valve body portion of a valve assembly through a separating wall residing therebetween. As the drive motor is not physically coupled to the valve body, the drive motor can be isolated from the valve body and from the working fluid of the valve assembly without the need for seals or other leak prone elements. Consequently, the risk of leakage and/or fire is substantially eliminated and the drive motor may be operated at maximum power and efficiency.

One embodiment of the present invention employs a pair of magnets to transmit torque from a drive motor to a valve body portion of the valve assembly. Each magnet is preferably a disk-shaped magnet that has been magnetized across its diameter, such that the pair of magnets is attracted into a specific orientation, but will repel each other under any other orientation. In this embodiment, rotation of the valve body is converted into linear movement by its threaded engagement with a stationary element—thereby greatly reducing any inaccuracies that may occur due to the use of a non-physically coupled linkage.

Preferably, the valve body is also provided with a valve body sensor magnet. This senor magnet is used to provide a feedback signal for the valve controller. A position sensor, such as a Hall Effect sensor is then located on or in the cylinder housing in proximity to the valve body sensor magnet. As the valve body is moved linearly within the cylinder by the drive motor during opening and closing of the valve, its position can be detected by the position sensor. Signals from the position sensor can be used by the electronic control system to regulate the position of the valve body and, consequently, fluid flow through the valve assembly and the amount of damping provided by the cylinder.

In order to maximize the coupling forces between the drive motor and the valve body, the respective magnets are preferably located in close proximity to one another. For example, the magnets may be separated by a thin wall of non-magnetic material. Small anti-friction projections may protrude from either the separating wall or the magnets in order to facilitate free rotation thereof.

A damping cylinder employing the valve assembly of the present invention may be of various design. However, in one particular embodiment, such a damping cylinder employs two separate valve assemblies of the present invention.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1a is a side view of a magnetically-coupled actuating valve assembly of the present invention, wherein the valve assembly includes its own housing and is shown in a closed position;

FIG. 1b is a side view of the magnetically-coupled actuating valve assembly of FIG. 1a, with the valve in an open position;

DETAILED DESCRIPTION OF THE EXEMPLARY EMBODIMENT(S)

One embodiment of a magnetically-coupled valve assembly 5 for an electronically controlled prosthetic knee can be seen in FIGS. 1–4. As shown in FIGS. 1–4, the valve assembly 5 resides within a housing 10. It should be understood that the housing 10 depicted in FIGS. 1–4 will typically consist of a portion of a cylinder housing to which the valve assembly 5 is installed (see FIG. 5). However, it is also possible that the valve assembly 5 may have its own housing (as illustrated in FIGS. 1–4), which may be of various cross-sectional shape. The housing 10 may be made of various materials of sufficient strength, but is preferably constructed of a metallic material such as steel, aluminum, or titanium.

Figure 2:
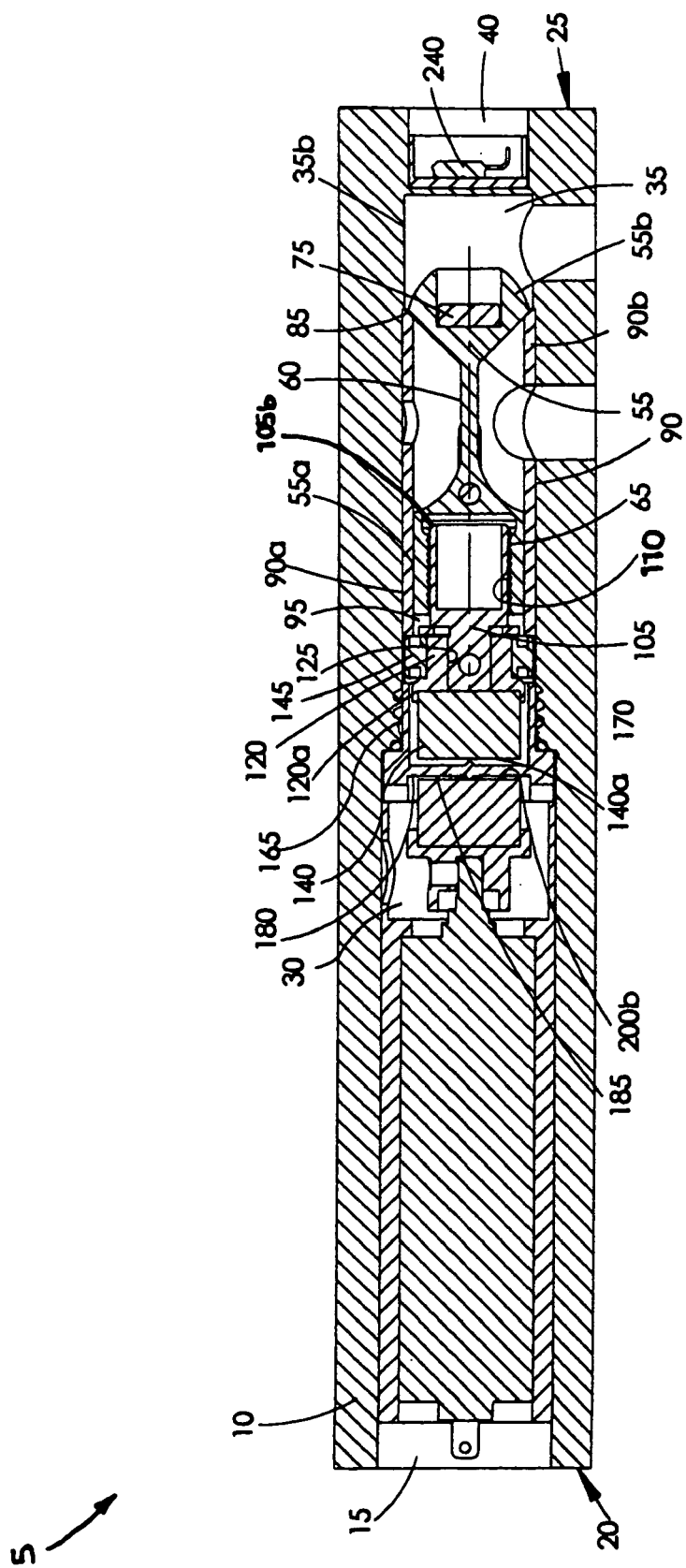
FIG. 2 is a cross-sectional top plan view of the magnetically-coupled actuating valve assembly of FIG. 1a, wherein the valve assembly is shown in a closed position.
Figure 3:
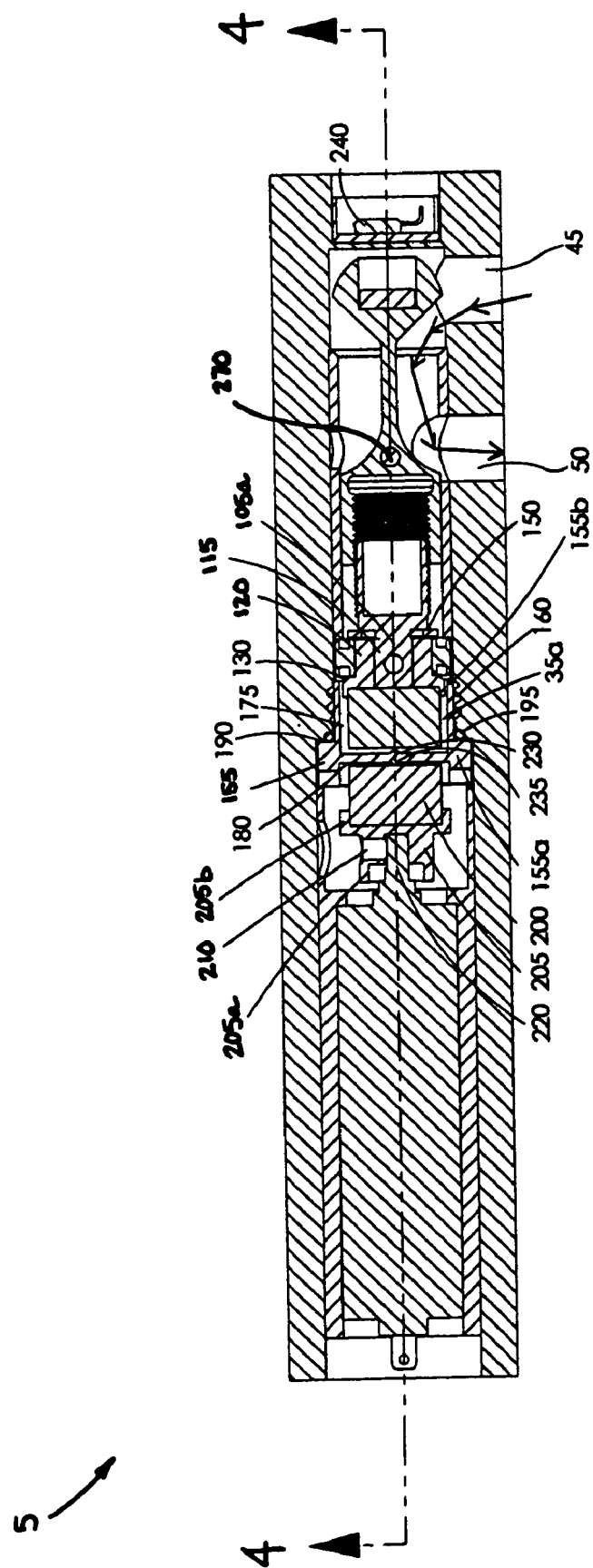
FIG. 3 is a cross-sectional top plan view of the magnetically-coupled actuating valve assembly of FIG. 1b, wherein the valve assembly is shown in an open position.
Figure 4:
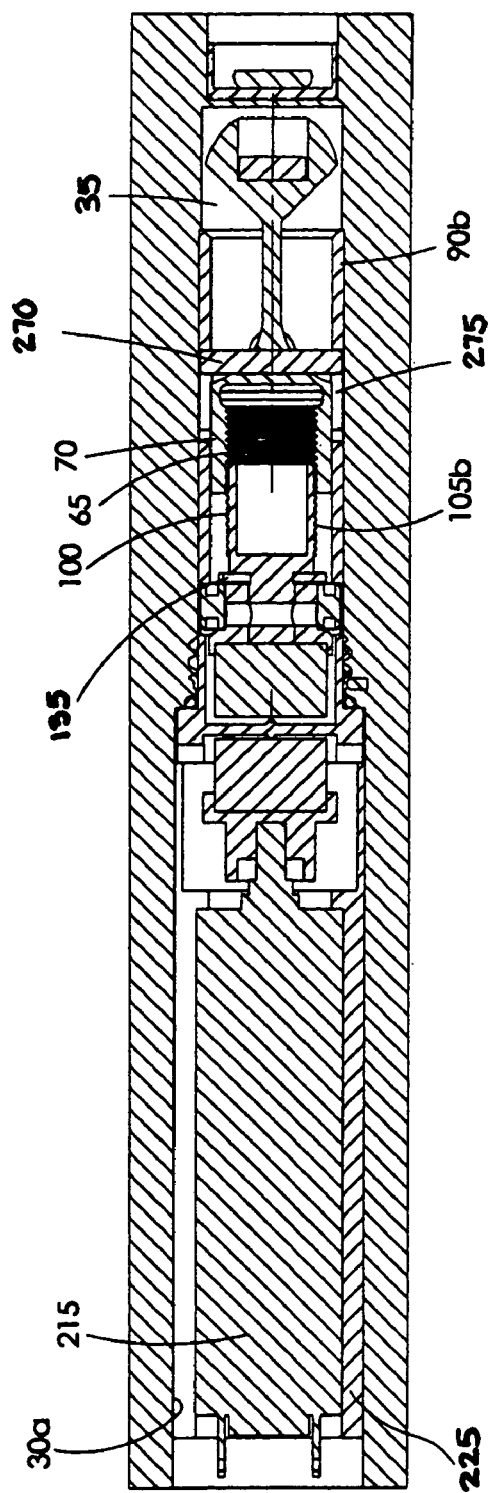
FIG. 4 is a cross-sectional side view of the magnetically-coupled actuating valve assembly of FIG. 3, wherein a valve pin and valve pin track are visible.

As can be best observed by reference to FIGS. 2–4, a central aperture 15 extends into the interior of the housing 10 from a first (proximal) end 20 thereof. The central aperture 15 of this embodiment is of varying diameter for accommodating the unique components of the valve assembly 5, although a central aperture of singular diameter may also be used. Generally speaking, a first section of the central aperture 15 forms a drive chamber 30 for accommodating the driving components of the valve assembly 5, while the remaining section of the central aperture forms a valve control chamber 35 for accommodating the valve components of the valve assembly.

Preferably, the central aperture 15 does not pass completely through the longitudinal length of the housing 10 but, instead, stops slightly short thereof (as best shown in FIGS. 2–4). In this manner, a sensor cavity 40 that is axially aligned with the central aperture 15 can be created by boring some distance into the housing 10 from a second (distal) end 25 thereof. This bore is preferably of a depth that permits a thin wall of valve body material to remain between the sensor cavity 40 and the central aperture 15. In an alternate embodiment, the central aperture 15 passes completely through the housing 10, and may be plugged at one or both ends, such as to form the receiving cavity 40, for example. In yet another embodiment, the central aperture 15 is formed by a pair of bores extending inward from each end 20, 25 of the housing 10. In this embodiment, the depth of the bores is preferably such that a thin separating wall of housing material remains therebetween.

An input port 45 and an output port 50 are also typically bored into the housing 10 so as to intersect the central aperture 15. Preferably, but not necessarily, the input port 45 and output port 50 are bored in a direction that is substantially transverse to the longitudinal axis of the central aperture 15.

In this particular embodiment of the valve assembly 5, the components residing within the valve control chamber 35 include: a valve body 55 and associated sensor magnet 75; a valve tube 90; a valve body driver 105; a valve driving magnet mount 120; a valve driving magnet 140; a valve cap 155; and a micro bearing 145. These components reside in, or at least partially in, the sealed valve control chamber 35.

As can be seen, the valve body 55 is essentially a spool that tapers from its proximal end 55a to its distal end 55b—although other profiles are also possible. The distal end 55b of the valve body 55 is preferably adapted to house the sensor magnet 75, and may optionally house an anti-friction pad (not shown). The anti-friction pad may have a projection that extends slightly beyond the distal end of the valve body 55 to prevent actual contact between the valve body and the wall of the valve control chamber 35. This embodiment of the valve body 55 is provided with an incurvate section 60 between its proximal and distal ends 55a, 55b to permit the passage of hydraulic fluid during operation of the valve assembly 5.

As can be best understood by reference to FIGS. 2–4, the valve body 55 is located in the valve control chamber 35 such that linear displacement thereof can be used to control the flow of fluid through the input and output ports 45, 50, as indicated by the arrows. More specifically, as the valve body 55 is moved toward a distal end 35b of the valve control chamber 35, the incurvate section 60 allows pressurized fluid to pass from the input port 45 to the output port 50, and through the valve control chamber. In contrast, as the valve body 55 is moved toward a proximal end 35a of the valve control chamber 35, its distal end 55b (portion) blocks the input port 45. Fluid flow can therefore be regulated or stopped by controlling the extent to which the input port 45 is blocked by the valve body 55. A tapered bushing 85 may be optionally located in the valve control chamber 35 to mate with the distal end 55b of the valve body 55 and provide a more secure seal when the valve assembly is in a closed position. Of course, the tapered bushing 85 may take on other shapes as necessary to provide a seal with a valve body of different profile.

The valve body 55 is provided with a threaded portion 65 near its proximal end 55a that is designed to engage a like-threaded portion of a valve body driver 105. The threaded portion 65 of the valve body 55 may have internal threads 70 of various pitch. It has been found, however, that decreasing the thread pitch (i.e., increasing the number of threads per inch) allows for more precise control over valve body 55 positioning during operation of the valve assembly 5.

The internal valve body threads 70 extend inward some distance from the proximal end 55*a* of the valve body 55. The internal valve body threads 70 are designed to engage mating external threads 110 located near the distal end 105*b* of the valve body driver 105. This engagement transfers the rotational motion of the valve body driver 105 into a linear motion that causes the valve body 55 to translate within the valve tube 90 and along the central axis of the valve control chamber 35. It is this linear displacement of the valve body 55 that is used to control the flow of pressurized fluid through the valve control chamber 35.

A guide means is preferably also provided to direct the linear movement of the valve body 55. In this embodiment of the present invention, a valve pin 270 preferably extends from the valve body 55, with at least one end thereof riding in a valve pin track 275, such as the slot shown in FIG. 4. In this particular embodiment, the valve pin track 275 is located in the valve tube 90. If no valve tube is employed, the valve pin track may also be located directly in the walls of the valve control chamber 35. The combination of the valve pin 270 and valve pin track 275 prevents rotation of the valve body 55 while simultaneously ensuring that the valve body moves linearly and substantially along the central axis of the valve chamber 35. Other means of prohibiting the rotation of and/or guiding the linear movement of the valve body 55 can also be employed, and alternate embodiments thereof are considered within the scope of the present invention.

This particular embodiment of the present invention employs a valve tube 90, although it is contemplated that the function provided thereby may also be accomplished by machining particular features into the walls of the valve control chamber 35. As shown, the valve tube 90 consists essentially of a substantially hollow cylinder having a proximal end 90*a* and a distal end 90*b*. The interior bore of the valve tube 90 is sized to receive the threadedly-engaged portions of the valve body 55 and the valve body driver 105. The valve tube 90 is preferably located within the valve control chamber 35 such that its distal end 90*b* does not block the output port 50. The valve tube 90 can be retained in position within the valve body 5 by means of a press-type fit, by a set screw, through use of an adhesive, or by a variety of other means.

A proximal end 105*a* of the valve body driver 105 forms a shaft 115 that is received by the valve driving magnet mount 120. The shaft 115 of the valve body driver 105 may be of various cross section, such as a circular or polygonal cross section, for example. Similarly, certain outer surfaces of the valve body driver 105 may be of various cross section—although forming the valve body driver in the shape of a cylinder having dissimilar diameters simplifies construction.

The valve driving magnet mount 120 is also preferably of circular outer cross section. The valve driving magnet mount 120 has an aperture 125 that passes at least partially therethrough along its longitudinal axis. The aperture 125 is provided to receive the shaft 115 of the valve body driver 105. The shaft 115 of the valve body driver 105 may be coupled to the valve driving magnet mount 120 by means of a pin, a spring-loaded ball, an adhesive, or any of various other suitable retaining methods. It is desired that the shaft 115 of the valve body driver 105 be prohibited from both rotation and linear displacement within the valve driving magnet mount 120.

A proximal end 120*a* of the valve driving magnet mount 120 is adapted to receive a portion of the valve driving magnet 140. The valve driving magnet mount 120 preferably rotates within a micro-bearing 145 located between its outer surface and the wall of the valve control chamber 35. The micro-bearing 145 may be at least partially trapped between or within the proximal end 90*a* of the valve tube 90 and a shoulder 130 formed about the outside of the valve driving magnet mount 120. Preferably, a bearing retainer ring 150 is also located in a gap between the distal end 120*b* of the valve driving magnet mount 120 and a shoulder 135 formed on the outside of the valve body driver 105, thereby ensuring there is no linear displacement of the micro-bearing 145.

The valve driving magnet 140 is affixed to the proximal end 120*a* of the valve driving magnet mount 120. In this embodiment, the valve driving magnet 140 is comprised of a disk of magnetic material of some predetermined thickness. Various magnetic materials can be used for this purpose. The valve driving magnet 140 can be attached to the valve driving magnet mount 120 by any number of means, although it has been discovered that a high-strength epoxy adhesive works well for this purpose.

In this embodiment, the valve control chamber 35 is separated and sealed from a drive chamber 30 by a valve cap 155. A distal portion 155*b* of the valve cap 155 has a threaded outer surface 160 to engage a like threaded section 165 at the proximal end 35*a* of the valve control chamber 35. A proximal portion 155*a* of the valve cap 155 is preferably of larger diameter than the distal portion 155*b*, such that an exterior shoulder 170 is formed at the intersection thereof. When properly installed, the shoulder 170 of the valve cap 155 is designed to abut a shoulder 190 formed in the housing 10 at the intersection of the valve control chamber 35 and drive chamber 30. As such, after installation, the distal portion 155*b* of the valve cap 155 will reside in the valve control chamber 35, while the proximal portion 155*a* will reside in the drive chamber 30. Although fully threading the valve cap 155 into the valve control chamber 35 may provide an adequate seal, it is preferred that an o-ring 195 or a similar sealing element be installed between the shoulder 170 on the valve cap 155 and the shoulder 190 in the housing 10. In this manner, it can be substantially ensured that fluid from the valve control chamber 35 cannot pass into the drive chamber 30 once all the components are properly installed in the housing 10.

The distal portion 155*b* of the valve cap 155 also contains an internal valve driving magnet chamber 175 that permits the valve driving magnet 140 to rotate therein. Although not essential, in the particular embodiment shown, the valve driving magnet chamber 175 is of sufficient diameter to receive at least a portion of the proximal end 120*a* of the valve driving magnet mount 120, and to permit rotation thereof along with the valve driving magnet 140. A recess 180 is preferably, but not necessarily, located in the proximal end 155*a* of the valve cap 155. The recess 180 is provided to reduce the gap between the valve driving magnet 140 and a motor driven magnet 200 that resides in the drive chamber 30. The recess 180 may be of a diameter that is similar or dissimilar to the diameter of the valve driving magnet chamber 175. Preferably, however, the recess 180 and the valve driving magnet chamber 175 are substantially axially aligned.

In this embodiment, the internal valve driving magnet chamber 175 and the recess 180 are of a depth such that only a thin separating wall 185 of valve cap material exists therebetween. Magnetic coupling forces will pass between the magnets 140, 200 and through the separating wall 185 during operation of the valve assembly 5. Because both the motor driven magnet 200 and the valve driving magnet 140 will rotate in close proximity to portions of the valve cap 155, it is preferred that the valve cap be produced from a nonmagnetic material.

In order to further promote free rotation of the motor driven magnet 200 and the valve driving magnet 140, friction-reducing projections 230, 235 are preferably located therebetween. In this embodiment, the friction-reducing projections 230, 235 extend from each side of the separating wall 185. Alternatively, the friction-reducing projections 230, 235 could also extend from adjacent sides 140a, 200b of each magnet 140, 200. In either case, the friction-reducing projections provide for a minimal contact area between the separating wall 185 and the magnets 140, 200. More specifically, aside from their points of contact, the friction-reducing projections 230, 235 produce a slight gap between the magnets 140, 200 and the separating wall 185, thereby preventing any substantial surface-to-surface contact from occurring therebetween during rotation. Use of the friction-reducing projection 230 on the valve control chamber 35 side of the separating wall 185 also prohibits a liquid shear film from developing between the separating wall and a proximal surface 140a of the valve driving magnet 140.

In this particular embodiment of the valve assembly 5, the components residing within the drive chamber 30 consist essentially of: a motor driven magnet 200; a driven magnet mount 205; a drive motor 215; and a motor lock and spacing sleeve 225. As can be best observed in FIGS. 2–4, proper installation of these components preferably results in a minimal spacing between the magnets 140, 200.

A proximal portion 30a of the drive chamber 30 is designed to retain the drive motor 215. The proximal portion 30a of the drive chamber 30 is preferably of slightly greater diameter than the drive motor 215 which will be installed thereto, such that the motor locking and spacing sleeve 225 can be located between the outside surface of the drive motor and the wall of the drive chamber. The motor locking and spacing sleeve 225 ensures the proper location of the drive motor 215 within the drive chamber 30, and also prevents rotation of the drive motor when under power. In this particular embodiment the drive motor 215 is positioned so that its connecting terminals extend from the proximal end 20 of the housing 10. Although, it should be realized that the connecting terminals could also be located within the housing 10.

The particular drive motor 215 used may depend on the design of the actuator to which the valve assembly 5 will be installed. Preferably, any motor employed will be small in overall size, lightweight, and require minimal energy for operation. To this end, different types of DC motors, such as a brush-type DC motor, brushless DC motor, and DC stepper motor, have proved acceptable for use as a drive motor 215 of the present invention.

Preferably, the drive motor 215 is also coupled to a speed reducer that converts the generally high rotational speed of the drive motor to a more usable output speed. In this particular embodiment of the present invention, a gearhead is integrated into the motor design and is, therefore, not separately visible. However, the speed reducer may also be a separate unit that is coupled to the output shaft of the drive motor 215. Alternatively, a drive motor 215 of low speed/high torque design may be employed, wherein a speed reducer is not required.

As shown, a proximal end 205a of the driven magnet mount 205 is coupled to the output shaft 220 of the drive motor 215 (gearhead). Like the valve driving magnet mount 120, the driven magnet mount 205 is also preferably, but not necessarily, of circular outer cross section. In this particular embodiment, the driven magnet mount 205 is affixed to the output shaft 220 of the drive motor 215 by means of a set screw 210, although other means of securing the magnet mount 205 to the output shaft 220 of the drive motor 215 may also be employed, and such would be understood by one skilled in the art. The distal end 205b of the driven magnet mount 205 is adapted to receive the motor driven magnet 200.

The motor driven magnet 200 of this embodiment is shown to be of similar size and shape to the valve driving magnet 140, although such is not required. The motor driven magnet 200 may be formed from various magnetic materials, so long as the material results in a sufficient magnetic attraction to the valve driving magnet 140. The motor driven magnet 200 can be attached to the driven magnet mount 205 by any number of means, although it has been discovered that a high-strength epoxy adhesive works well for this purpose.

Proper design and assembly of the motor driven magnet 200 and driven magnet mount 205 to the drive motor 215 preferably results in location of the motor driven magnet within close proximity to the valve driving magnet 140. As shown in this particular embodiment of the valve assembly 5, the distal end (surface) 200b of the motor driven magnet 200 resides within the recess 180 in the valve cap 155 and is, therefore, separated from the valve driving magnet 140 only by the separating wall 185 and the small gaps produced by the friction-reducing projections 230, 235. As discussed above, the drive-side friction-reducing projection 235 is preferably located between the separating wall 185 and the motor driven magnet 200 to reduce frictional forces therebetween.

In operation, electrical energy is provided to the drive motor 215 from a source such as a battery or a capacitor, for example. Subsequent rotation of the drive motor output shaft 220 causes a corresponding rotation of the driven magnet mount 205 and the motor driven magnet 200 attached thereto. Due to the magnetic field existing between the motor driven magnet 200 and the valve driving magnet 140, the valve driving magnet and the valve body driver 105 attached thereto will also rotate in conjunction with the motor driven magnet. Due to use of the valve pin 270 and valve pin track 275, rotation of the valve body driver 105 causes a linear displacement of the valve body 55 along the longitudinal axis of the valve control chamber 35. The direction of rotation of the drive motor 215 determines whether the valve body 55 is moved toward the distal end 35b or proximal end 35a of the valve control chamber 35, thereby opening or restricting the input port 45.

Fluid flow through the input and output ports 45, 50 can be precisely regulated by controlling the position of the valve body 55 with respect to the input port. In order to detect and control the linear position of the valve body 55, a position sensor 240 is preferably mounted at the distal end 25 of the housing 10. In this particular embodiment of the present invention, the position sensor 240 is comprised of a Hall Effect sensor—although other types of sensors familiar to one skilled in the art could also be employed. The Hall Effect sensor 240 is shown to be mounted within the sensor cavity 40 in the distal end 25 of the housing 10. The sensor cavity 40 is preferably of a depth such that only a thin wall of material resides between the cavity and the distal end 35b of the valve control chamber 35. Depending on the design of the valve assembly, the position sensor(s) may also be located at other locations thereon, as may a cavity for receiving the position sensor.

In the embodiment shown, valve body position feedback is provided by using the Hall Effect sensor 240 to detect the location of the sensor magnet 75 mounted in the distal end 55b of the valve body 55. The readings provided by the Hall Effect sensor 240 will vary with the position of the sensor magnet 75 within the detection field of the Hall Effect sensor. Thus, these readings can be correlated with specific valve body positions by an electronic control system in communication with the valve assembly 5 and can, therefore, be used to control the position of the valve body 55 and the flow of pressurized fluid through the cylinder to which the valve assembly is installed.

Figure 5:
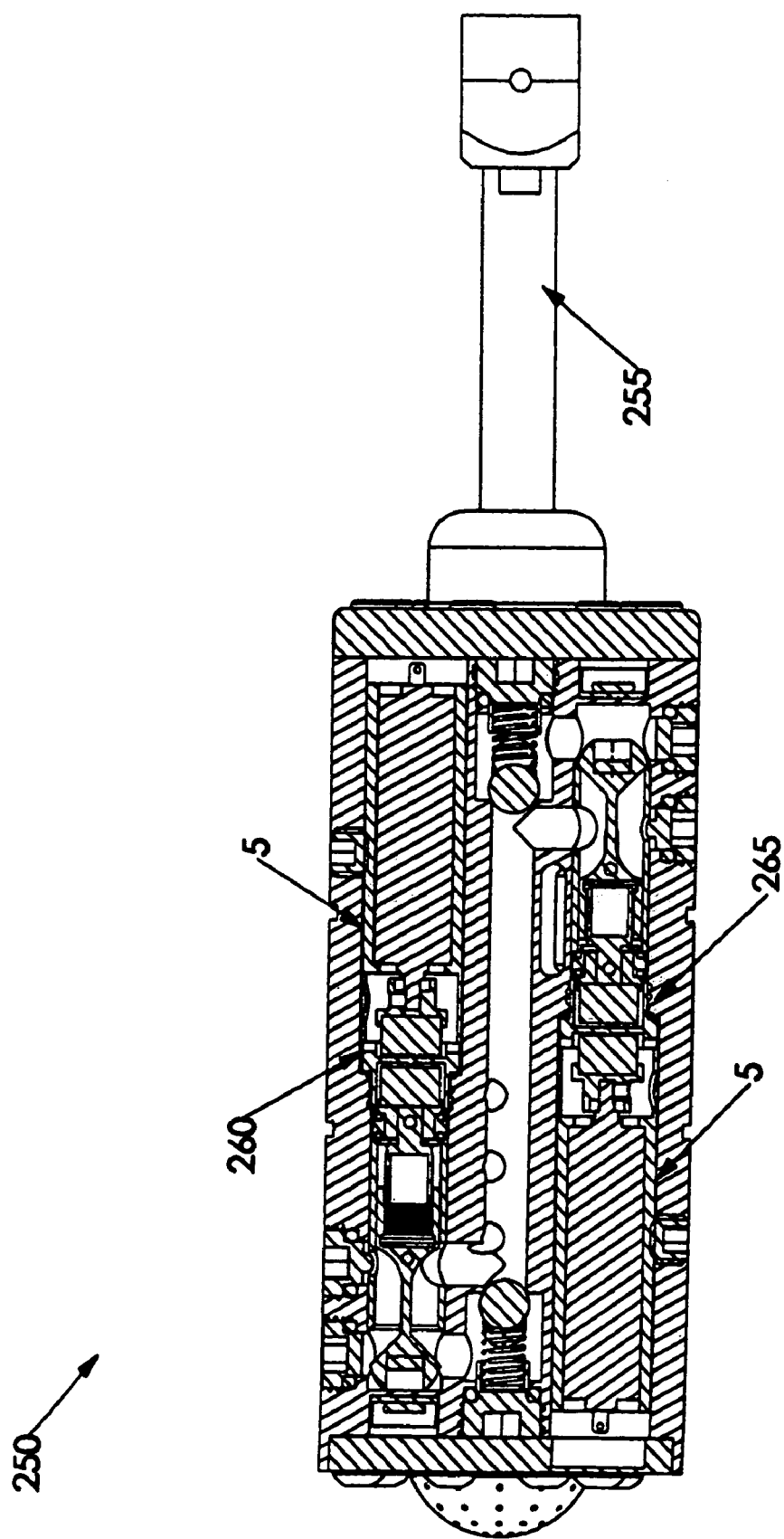
FIG. 5 is a cross-sectional side view of an exemplary damping cylinder that employs two magnetically-coupled actuating valve assemblies of the present invention.

One embodiment of a damping cylinder 250 utilizing the valve assembly 5 of the present invention is illustrated in FIG. 5. This particular damping cylinder 250 actually makes use of two separate valve assemblies 5 to provide for control over extension and retraction of the cylinder rod 255. This cylinder 250 can be used in an electronically controlled prosthetic knee to regulate knee movement.

When used in a prosthetic knee, the flexion control valve 260 acts to regulate the flow of working fluid expelled from below the piston (not shown) of the cylinder 250 during the flexion (bending) phase of an amputee's gait cycle, thereby providing for a controlled damping of knee flexion. Similarly, during the extension phase of an amputee's gait cycle, the extension control valve 265 acts to regulate the flow of working fluid expelled from above the piston of the cylinder 250—thereby providing for a controlled damping of knee extension.

Figure 6:
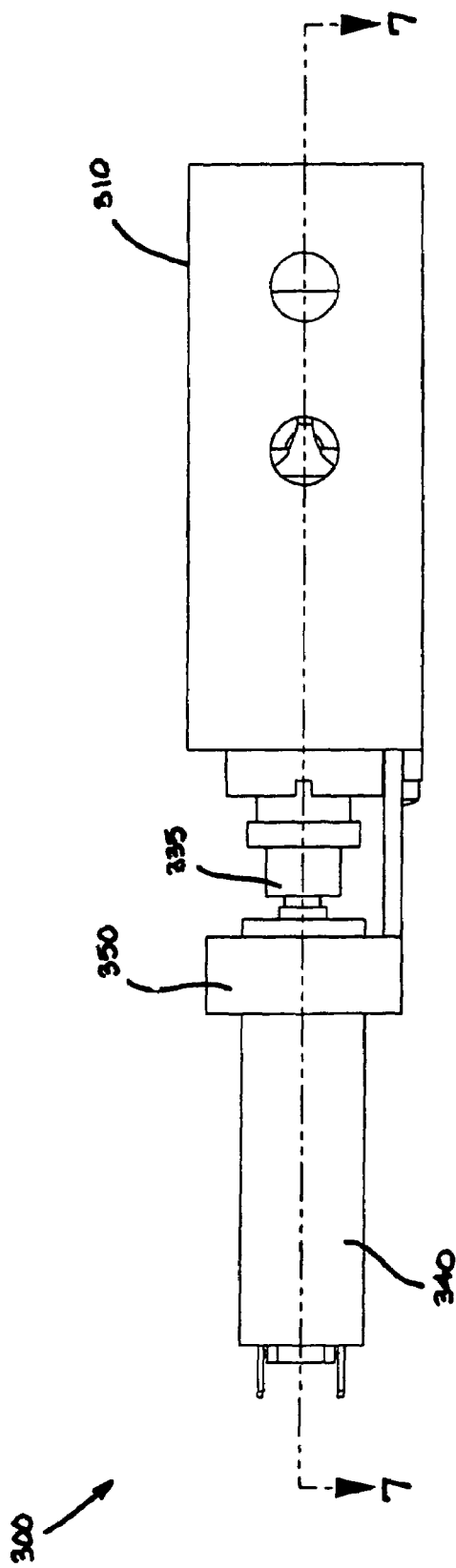
FIG. 6 is a side view of an alternate embodiment of a magnetically-coupled actuating valve assembly of the present invention, wherein a drive motor portion is external to a housing portion thereof.
Figure 7:
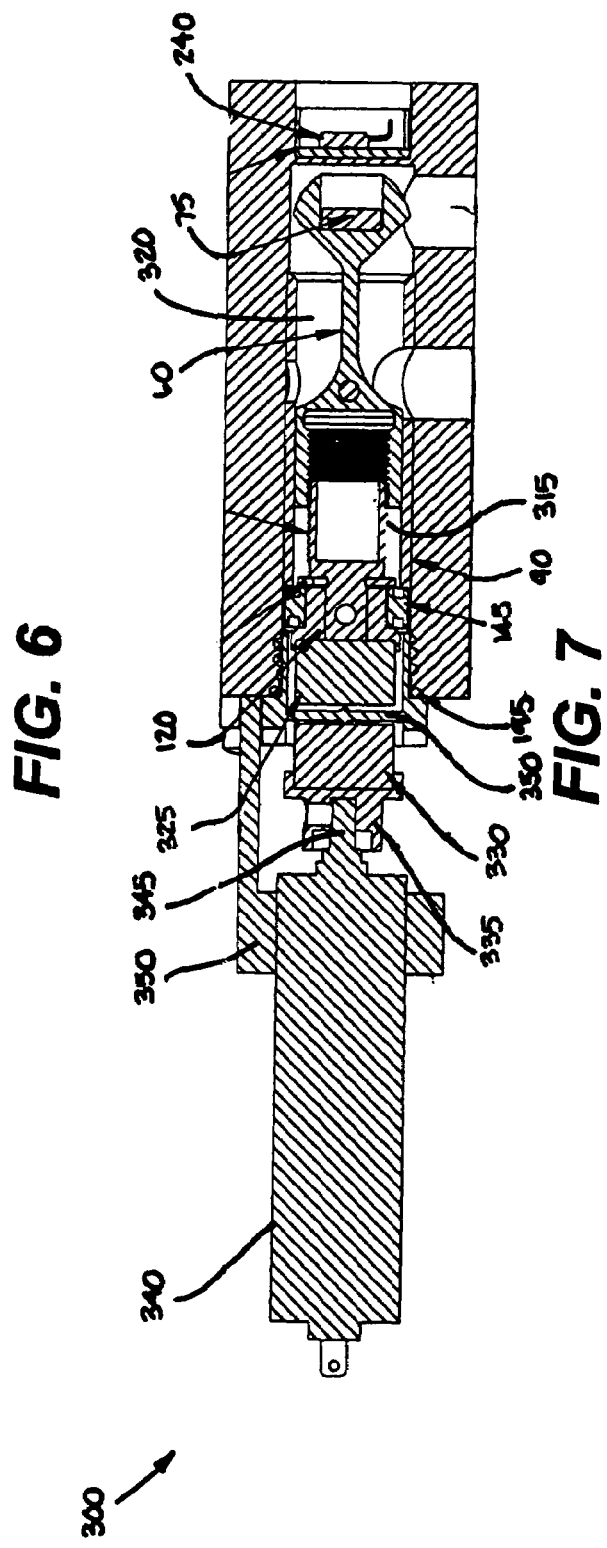
FIG. 7 is a cross-sectional top plan view of the magnetically-coupled actuating valve assembly of FIG. 6.

An alternate embodiment of a magnetically-coupled valve assembly 300 of the present invention is depicted in FIGS. 6–7. As can be seen, a valve control chamber 320 is again formed by a housing 310 having a central aperture 315. The design and construction of this portion of the valve assembly 300 is essentially the same as that of the valve assembly 5 shown in FIGS. 1–5, and is shown to include the same internal components. Consequently, operation of this portion of the valve assembly 300, as well as the overall operation of the valve assembly, can be understood by reference to the foregoing description of the previously described valve assembly 5.

Unlike the valve assembly 5 depicted in FIGS. 1–6, however, in this embodiment of the valve assembly 300 the drive motor 340 does not reside within a drive chamber that is also internal to the housing 315. Rather, the drive motor 340 is mounted by a motor mount 350 to the exterior of the housing 315 at a proximal end 315a thereof.

The orientation and location of the drive motor 340 preferably places its output shaft 345 near the location of the valve driving magnet 325 that resides within the valve control chamber 320. The drive motor 340 is then coupled to the valve driving magnet 325 by a motor driven magnet 330 that is attached to the output shaft 345 of the drive motor 340 by means of a driven magnet mount 335. The magnets 325, 330 may again be separated by a separating wall 350, and any of the aforementioned techniques for reducing friction with regard to the rotating magnets may also be employed herein.

It should be understood that a valve assembly of the present invention may be integrated into actuators for use in fields other than prosthetics. It should also be understood that the valve assemblies shown are for purposes of illustration only, and the invention is not considered limited to the specific design or components illustrated or described with respect thereto. Thus, while certain embodiments of the present invention are described in detail above, the scope of the invention is not to be considered limited by such disclosure, and modifications are possible without departing from the spirit of the invention as evidenced by the following claims:

What is claimed is:

1. A magnetically-coupled actuating valve assembly for controlling an actuator, comprising:
   a housing having a valve control chamber and a drive chamber isolated from one another by a separating wall;
   a valve body coupled to a first magnet within said valve control chamber and a drive motor coupled to a second magnet within said drive chamber, said first magnet magnetically coupled to said second magnet through said separating wall; and
   a means for converting rotation of said magnets into linear displacement of said valve body within said valve control chamber;
   wherein said linear movement is operative to place a portion of said valve body into communication with an inlet port and to control a flow of working fluid through said valve control chamber.

2. The magnetically-coupled actuating valve of claim 1, wherein said housing comprises a portion of said actuator.

3. The magnetically-coupled actuating valve of claim 1, wherein said separating wall includes a recess on either side thereof for receiving a portion of said first and second magnets.

4. The magnetically-coupled actuating valve of claim 1, wherein said separating wall includes a projection on either side thereof, said projection minimizing the contact area between said separating wall and each magnet and thereby facilitating rotation thereof.

5. The magnetically-coupled actuating valve of claim 1, wherein said separating wall comprises a portion of said housing.

6. The magnetically-coupled actuating valve of claim 1, wherein said separating wall comprises a valve cap that is installed into said valve control chamber.

7. The magnetically-coupled actuating valve of claim 6, further comprising an o-ring that works in conjunction with said valve cap to seal said valve control chamber from said drive chamber.

8. The magnetically-coupled actuating valve of claim 1, wherein said valve body is constrained from rotation, said valve body engaged with a drive element that is coupled to said second magnet, such that rotation of said drive element by said second magnet causes a linear displacement of said valve body within said valve control chamber.

9. The magnetically-coupled actuating valve of claim 8, further comprising a guide means for directing the linear displacement of said valve body substantially along the longitudinal axis of said valve control chamber.

10. The magnetically-coupled actuating valve of claim 9, wherein said guide means comprises a pin that extends from said valve body into a longitudinally oriented guiding slot.

11. The magnetically-coupled actuating valve of claim 1, further comprising a projection extending from a distal end of said valve body, said projection minimizing the contact area between a wall of said valve control chamber and said valve body and thereby facilitating rotation thereof.

12. The magnetically-coupled actuating valve of claim 1, further comprising a bearing for facilitating rotation of said valve body.

13. The magnetically-coupled actuating valve of claim 1, further comprising a speed reducer associated with said drive motor.

14. The magnetically-coupled actuating valve of claim 1, further comprising a position sensor located in proximity to a distal end of said valve control chamber, said position sensor for determining and controlling the position of said valve body.

15. The magnetically-coupled actuating valve of claim 14, wherein said position sensor is a Hall Effect sensor.

16. The magnetically-coupled actuating valve of claim 14, further comprising a magnet located in a distal portion of said valve body, said magnet interacting with said position sensor to determine and control the position of said valve body.

17. The magnetically-coupled actuating valve of claim 1, further comprising a sealing bushing for mating with said valve body and helping to prevent working fluid from flowing from said input port to said output port.

18. The magnetically-coupled actuating valve of claim 1, wherein said actuator is a damping cylinder for use in a prosthetic limb.

19. The magnetically-coupled actuating valve of claim 18, wherein said prosthetic limb is an electronically controlled prosthetic knee.

20. A magnetically-coupled actuating valve assembly for controlling an actuator, comprising:
   a housing having a drive chamber and a valve control chamber isolated from one another by a separating wall;
   at least one input port and at least one output port in communication with said valve control chamber;
   a motor driven magnet in said drive chamber magnetically coupled to a valve driving magnet in said valve control chamber through said separating wall;
   a drive motor residing within said drive chamber and coupled to said motor driven magnet such that rotation of said drive motor produces a corresponding rotation of said motor driven magnet and said valve driving magnet; and
   a valve body residing within said valve control chamber, said valve body constrained against rotation within said valve control chamber, said valve body engaged with a drive element coupled to said valve driving magnet, such that rotation of said drive element by said valve driving magnet produces a linear displacement of said valve body substantially along the longitudinal axis of said valve control chamber;
   wherein said linear movement allows for variable communication between a portion of said valve body and said inlet port and for resulting control over an amount of working fluid entering said valve control chamber therethrough.

21. The magnetically-coupled actuating valve of claim 20, wherein said housing comprises a portion of said actuator.

22. The magnetically-coupled actuating valve of claim 20, wherein said separating wall includes a recess on either side thereof for receiving a portion of said motor driven magnet and said valve driving magnet, respectively.

23. The magnetically-coupled actuating valve of claim 20, wherein said separating wall includes a projection on either or both sides thereof, said projection minimizing the contact area between said separating wall and each magnet and thereby facilitating rotation thereof.

24. The magnetically-coupled actuating valve of claim 20, wherein said separating wall comprises a portion of said housing.

25. The magnetically-coupled actuating valve of claim 20, wherein said separating wall comprises a valve cap that is threaded into said valve control chamber.

26. The magnetically-coupled actuating valve of claim 25, further comprising an o-ring that works in conjunction with said valve cap to seal said valve control chamber from said drive chamber.

27. The magnetically-coupled actuating valve of claim 20, wherein said valve body is threadedly engaged with said drive element.

28. The magnetically-coupled actuating valve of claim 20, further comprising a guide means for directing the linear displacement of said valve body substantially along the longitudinal axis of said valve control chamber.

29. The magnetically-coupled actuating valve of claim 28, wherein said guide means comprises a pin that extends from said valve body into a longitudinally oriented guiding slot.

30. The magnetically-coupled actuating valve of claim 20, further comprising a projection extending from a distal end of said valve body, said projection minimizing the contact area between a wall of said valve control chamber and said valve body and thereby facilitating rotation thereof.

31. The magnetically-coupled actuating valve of claim 20, further comprising a bearing within said valve control chamber for facilitating rotation of said valve body.

32. The magnetically-coupled actuating valve of claim 20, further comprising a speed reducer associated with said drive motor.

33. The magnetically-coupled actuating valve of claim 20, further comprising a position sensor located in proximity to a distal end of said valve control chamber, said position sensor for determining and controlling the position of said valve body.

34. The magnetically-coupled actuating valve of claim 33, wherein said position sensor is a Hall Effect sensor.

35. The magnetically-coupled actuating valve of claim 33, further comprising a magnet located in a distal portion of said valve body, said magnet interacting with said position sensor to determine and control the position of said valve body.

36. The magnetically-coupled actuating valve of claim 20, further comprising a sealing bushing for mating with said valve body and helping to prevent working fluid from flowing from said input port to said output port.

37. The magnetically-coupled actuating valve of claim 20, wherein said actuator is a damping cylinder for use in a prosthetic limb.

38. The magnetically-coupled actuating valve of claim 37, wherein said prosthetic limb is an electronically controlled prosthetic knee.

39. A magnetically-coupled actuating valve assembly for controlling an actuator, comprising:
   a housing having a drive chamber and a valve control chamber;
   a valve cap threaded into a proximal end of said valve control chamber, said valve cap forming a separating wall that isolates said drive chamber from said valve control chamber;
   at least one input port and at least one output port in communication with said valve control chamber;
   a motor driven magnet located in said drive chamber and a valve driving magnet located in said valve control chamber, such that said magnets are magnetically coupled to one another through said separating wall;
   a drive motor residing within said drive chamber and coupled to said motor driven magnet such that rotation of said drive motor produces a corresponding rotation of said motor driven magnet and said valve driving magnet;

a substantially hollow valve tube secured within said valve control chamber;

a valve body driver having a proximal end coupled to said valve driving magnet so as to rotate therewith, and a distal end residing within said valve tube and threadedly engaged with a valve body;

a valve body residing within said valve control chamber, said valve body having a distal portion that communicates with said inlet port, a middle portion that allows for passage of a working fluid, and a proximal portion that resides within said valve tube and is threadedly engaged with said valve body driver;

a means of constraining said valve body against rotation;

a position sensor for detecting the position of said valve body; and an electronic control system in communication with said position sensor and said drive motor;

wherein the threaded engagement of said valve body with said valve body driver operates to convert rotation of said valve body driver into a linear displacement of said valve body along the longitudinal axis of said valve control chamber, thereby allowing said electronic control system to variably control the amount of communication between said distal portion of said valve body and said inlet port, and to thereby control the amount of working fluid entering said valve control chamber therethrough.

40. The magnetically-coupled actuating valve of claim 39, wherein said housing comprises a portion of said actuator.

41. The magnetically-coupled actuating valve of claim 39, wherein said separating wall includes a recess on either side thereof for receiving a portion of said motor driven magnet and said valve driving magnet, respectively.

42. The magnetically-coupled actuating valve of claim 39, wherein said separating wall includes a projection on either side thereof, said projection minimizing the contact area between said separating wall and each magnet and thereby facilitating rotation thereof.

43. The magnetically-coupled actuating valve of claim 39, further comprising a projection extending from said motor driven magnet, said projection minimizing the contact area between said separating wall and said motor driven magnet and thereby facilitating rotation thereof.

44. The magnetically-coupled actuating valve of claim 39, further comprising a projection extending from said valve driving magnet, said projection minimizing the contact area between said separating wall and said valve driving magnet and thereby facilitating rotation thereof.

45. The magnetically-coupled actuating valve of claim 39, further comprising an o-ring that works in conjunction with said valve cap to seal said valve control chamber from said drive chamber.

46. The magnetically-coupled actuating valve of claim 39, further comprising a projection extending from a distal end of said valve body, said projection minimizing the contact area between a wall of said valve control chamber and said valve body and thereby facilitating rotation thereof.

47. The magnetically-coupled actuating valve of claim 39, further comprising a bearing within said valve control chamber for facilitating rotation of said valve body.

48. The magnetically-coupled actuating valve of claim 39, further comprising a speed reducer associated with said drive motor.

49. The magnetically-coupled actuating valve of claim 39, further comprising a position sensor located in proximity to a distal end of said valve control chamber.

50. The magnetically-coupled actuating valve of claim 49, wherein said position sensor is a Hall Effect sensor.

51. The magnetically-coupled actuating valve of claim 49, further comprising a magnet located in a distal portion of said valve body, said magnet interacting with said position sensor for indicating the position of said valve body.

52. The magnetically-coupled actuating valve of claim 39, further comprising a sealing bushing for mating with said valve body and helping to prevent working fluid from flowing from said input port to said output port.

53. The magnetically-coupled actuating valve of claim 39, wherein said actuator is a damping cylinder for use in a prosthetic limb.

54. The magnetically-coupled actuating valve of claim 53, wherein said prosthetic limb is an electronically controlled prosthetic knee.

55. The magnetically-coupled actuating valve of claim 39, further comprising a guide means for directing the linear displacement of said valve body substantially along the longitudinal axis of said valve control chamber.

56. The magnetically-coupled actuating valve of claim 55, wherein said guide means comprises a pin that extends from said valve body into a longitudinally oriented guiding slot located in said valve tube.

57. The magnetically-coupled actuating valve of claim 56, wherein said pin also acts to constrain said valve body against rotation.

58. A magnetically-coupled actuating valve assembly for controlling an actuator, comprising:

a housing having a valve body coupled to a first magnet within a valve control chamber located therein;

a drive motor coupled to a second magnet, said drive motor attached to an exterior of said housing such that said second magnet is magnetically coupled to said first magnet through a separating wall; and a means for converting rotation of said magnets into linear displacement of said valve body within said valve control chamber;

wherein said linear movement is operative to place a portion of said valve body into communication with an inlet port and to control a flow of working fluid through said valve control chamber.

59. The magnetically-coupled actuating valve of claim 58, wherein said housing comprises a portion of said actuator.

60. The magnetically-coupled actuating valve of claim 58, wherein said separating wall includes a recess on either side thereof for receiving a portion of said first and second magnets.

61. The magnetically-coupled actuating valve of claim 58, wherein said separating wall includes a projection on either side thereof, said projection minimizing the contact area between said separating wall and each magnet and thereby facilitating rotation thereof.

62. The magnetically-coupled actuating valve of claim 58, wherein said separating wall comprises a portion of said housing.

63. The magnetically-coupled actuating valve of claim 58, wherein said separating wall comprises a valve cap that is installed into said valve control chamber.

64. The magnetically-coupled actuating valve of claim 63, further comprising an o-ring that works in conjunction with said valve cap to seal said valve control chamber.

65. The magnetically-coupled actuating valve of claim 58, wherein said valve body is constrained from rotation, said valve body engaged with a drive element that is coupled to said second magnet such that rotation of said drive element by said second magnet causes a linear displacement of said valve body within said valve control chamber.

66. The magnetically-coupled actuating valve of claim 65, further comprising a guide means for directing the linear displacement of said valve body substantially along the longitudinal axis of said valve control chamber.

67. The magnetically-coupled actuating valve of claim 66, wherein said guide means comprises a pin that extends from said valve body into a longitudinally oriented guiding slot.

68. The magnetically-coupled actuating valve of claim 58, further comprising a projection extending from a distal end of said valve body, said projection minimizing the contact area between a wall of said valve control chamber and said valve body and thereby facilitating rotation thereof.

69. The magnetically-coupled actuating valve of claim 58, further comprising a bearing for facilitating rotation of said valve body.

70. The magnetically-coupled actuating valve of claim 58, further comprising a speed reducer associated with said drive motor.

71. The magnetically-coupled actuating valve of claim 58, further comprising a position sensor located in proximity to a distal end of said valve control chamber, said position sensor for determining and controlling the position of said valve body.

72. The magnetically-coupled actuating valve of claim 71, wherein said position sensor is a Hall Effect sensor.

73. The magnetically-coupled actuating valve of claim 71, further comprising a magnet located in a distal portion of said valve body, said magnet interacting with said position sensor to determine and control the position of said valve body.

74. The magnetically-coupled actuating valve of claim 58, further comprising a sealing bushing for mating with said valve body and helping to prevent working fluid from flowing from said input port to said output port.

75. The magnetically-coupled actuating valve of claim 58, wherein said actuator is a damping cylinder for use in a prosthetic limb.

76. The magnetically-coupled actuating valve of claim 75, wherein said prosthetic limb is an electronically controlled prosthetic knee.

77. A magnetically-coupled actuating valve assembly for controlling an actuator, comprising:
 a housing having a valve control chamber located therein;
 at least one input port and at least one output port in communication with said valve control chamber;
 a valve body residing within said valve control chamber, said valve body constrained against rotation within said valve control chamber and connected to a distal end of a drive element also located within said valve control chamber;
 a valve driving magnet located within said valve control chamber, said valve driving magnet attached to a proximal end of said drive element such that rotation of said valve driving magnet produces a linear displacement of said valve body substantially along the longitudinal axis of said valve control chamber; and
 a drive motor coupled to a motor driven magnet and attached to an exterior of said housing such that said motor driven magnet is magnetically coupled to said valve driving magnet through said separating wall;
 wherein rotation of said motor driven magnet by said drive motor produces a corresponding rotation of said valve driving magnet; and
 wherein the resulting linear movement of said valve body allows for variable communication between a portion of said valve body and said inlet port and for resulting control over an amount of working fluid entering said valve control chamber therethrough.

78. The magnetically-coupled actuating valve of claim 77, wherein said housing comprises a portion of said actuator.

79. The magnetically-coupled actuating valve of claim 77, wherein said separating wall includes a recess on either side thereof for receiving a portion of said motor driven magnet and said valve driving magnet, respectively.

80. The magnetically-coupled actuating valve of claim 77, wherein said separating wall includes a projection on either or both sides thereof, said projection minimizing the contact area between said separating wall and each magnet and thereby facilitating rotation thereof.

81. The magnetically-coupled actuating valve of claim 77, wherein said separating wall comprises a portion of said housing.

82. The magnetically-coupled actuating valve of claim 77, wherein said separating wall comprises a valve cap that is threaded into said valve control chamber.

83. The magnetically-coupled actuating valve of claim 82, further comprising an o-ring that works in conjunction with said valve cap to seal said valve control chamber.

84. The magnetically-coupled actuating valve of claim 77, wherein said valve body is threadedly engaged with said drive element.

85. The magnetically-coupled actuating valve of claim 77, further comprising a guide means for directing the linear displacement of said valve body substantially along the longitudinal axis of said valve control chamber.

86. The magnetically-coupled actuating valve of claim 85, wherein said guide means comprises a pin that extends from said valve body into a longitudinally oriented guiding slot.

87. The magnetically-coupled actuating valve of claim 77, further comprising a projection extending from a distal end of said valve body, said projection minimizing the contact area between a wall of said valve control chamber and said valve body and thereby facilitating rotation thereof.

88. The magnetically-coupled actuating valve of claim 77, further comprising a bearing within said valve control chamber for facilitating rotation of said valve body.

89. The magnetically-coupled actuating valve of claim 77, further comprising a speed reducer associated with said drive motor.

90. The magnetically-coupled actuating valve of claim 77, further comprising a position sensor located in proximity to a distal end of said valve control chamber, said position sensor for determining and controlling the position of said valve body.

91. The magnetically-coupled actuating valve of claim 90, wherein said position sensor is a Hall Effect sensor.

92. The magnetically-coupled actuating valve of claim 90, further comprising a magnet located in a distal portion of said valve body, said magnet interacting with said position sensor to determine and control the position of said valve body.

93. The magnetically-coupled actuating valve of claim 77, further comprising a sealing bushing for mating with said valve body and helping to prevent working fluid from flowing from said input port to said output port.

94. The magnetically-coupled actuating valve of claim 77, wherein said actuator is a damping cylinder for use in a prosthetic limb.

95. The magnetically-coupled actuating valve of claim 94, wherein said prosthetic limb is an electronically controlled prosthetic knee.

96. A magnetically-coupled actuating valve assembly for controlling an actuator, comprising:
- a housing having a valve control chamber;
- a valve cap threaded into a proximal end of said valve control chamber, said valve cap forming a separating wall;
- at least one input port and at least one output port in communication with said valve control chamber;
- a substantially hollow valve tube secured within said valve control chamber;
- a valve driving magnet located in said valve control chamber;
- a valve body driver having a proximal end coupled to said valve driving magnet so as to rotate therewith, and a distal end residing within said valve tube and threadedly engaged with a valve body;
- a valve body residing within said valve control chamber, said valve body having a distal portion that communicates with said inlet port, a middle portion that allows for passage of a working fluid, and a proximal portion that resides within said valve tube and is threadedly engaged with said valve body driver;
- a means of constraining said valve body against rotation;
- a motor driven magnet coupled to a drive motor, said drive motor attached to an exterior of said housing such that said motor driven magnet is magnetically coupled to said valve driving magnet through said separating wall;
- a position sensor for detecting the position of said valve body; and
- an electronic control system in communication with said position sensor and said drive motor;
- wherein, due to the magnetic coupling therebetween, rotation of said drive motor and said motor driven magnet produces a corresponding rotation and said valve body driver and said valve driving magnet; and
- wherein the threaded engagement of said valve body with said valve body driver operates to convert rotation of said valve body driver into a linear displacement of said valve body along the longitudinal axis of said valve control chamber, thereby allowing said electronic control system to variably control the amount of communication between said distal portion of said valve body and said inlet port, and to thereby control the amount of working fluid entering said valve control chamber therethrough.

97. The magnetically-coupled actuating valve of claim 96, wherein said housing comprises a portion of said actuator.

98. The magnetically-coupled actuating valve of claim 96, wherein said separating wall includes a recess on either side thereof for receiving a portion of said motor driven magnet and said valve driving magnet, respectively.

99. The magnetically-coupled actuating valve of claim 96, wherein said separating wall includes a projection on either side thereof, said projection minimizing the contact area between said separating wall and each magnet and thereby facilitating rotation thereof.

100. The magnetically-coupled actuating valve of claim 96, further comprising a projection extending from said motor driven magnet, said projection minimizing the contact area between said separating wall and said motor driven magnet and thereby facilitating rotation thereof.

101. The magnetically-coupled actuating valve of claim 96, further comprising a projection extending from said valve driving magnet, said projection minimizing the contact area between said separating wall and said valve driving magnet and thereby facilitating rotation thereof.

102. The magnetically-coupled actuating valve of claim 96, further comprising an o-ring that works in conjunction with said valve cap to seal said valve control chamber from said drive chamber.

103. The magnetically-coupled actuating valve of claim 96, further comprising a projection extending from a distal end of said valve body, said projection minimizing the contact area between a wall of said valve control chamber and said valve body and thereby facilitating rotation thereof.

104. The magnetically-coupled actuating valve of claim 96, further comprising a bearing within said valve control chamber for facilitating rotation of said valve body.

105. The magnetically-coupled actuating valve of claim 96, further comprising a speed reducer associated with said drive motor.

106. The magnetically-coupled actuating valve of claim 96, further comprising a position sensor located in proximity to a distal end of said valve control chamber.

107. The magnetically-coupled actuating valve of claim 106, wherein said position sensor is a Hall Effect sensor.

108. The magnetically-coupled actuating valve of claim 106, further comprising a magnet located in a distal portion of said valve body, said magnet interacting with said position sensor for indicating the position of said valve body.

109. The magnetically-coupled actuating valve of claim 96, further comprising a sealing bushing for mating with said valve body and helping to prevent working fluid from flowing from said input port to said output port.

110. The magnetically-coupled actuating valve of claim 96, further comprising a guide means for directing the linear displacement of said valve body substantially along the longitudinal axis of said valve control chamber.

111. The magnetically-coupled actuating valve of claim 110, wherein said guide means comprises a pin that extends from said valve body into a longitudinally oriented guiding slot located in said valve tube.

112. The magnetically-coupled actuating valve of claim 111, wherein said pin also acts to constrain said valve body against rotation.

113. The magnetically-coupled actuating valve of claim 96, wherein said actuator is a damping cylinder for use in a prosthetic limb.

114. The magnetically-coupled actuating valve of claim 113, wherein said prosthetic limb is an electronically controlled prosthetic knee.

* * * * *